(12) United States Patent
Averbuch

(10) Patent No.: US 10,292,619 B2
(45) Date of Patent: May 21, 2019

(54) PATIENT BREATHING MODELING

(75) Inventor: Dorian Averbuch, Ramat HaSharon (IL)

(73) Assignee: COVIDIEN LP, Mansfield, MA (US)

( * ) Notice: Subject to any disclaimer, the term of this patent is extended or adjusted under 35 U.S.C. 154(b) by 1945 days.

(21) Appl. No.: 12/170,385

(22) Filed: Jul. 9, 2008

(65) Prior Publication Data
US 2009/0156951 A1 Jun. 18, 2009

Related U.S. Application Data

(60) Provisional application No. 60/948,640, filed on Jul. 9, 2007, provisional application No. 61/043,987, filed on Apr. 10, 2008.

(51) Int. Cl.
| | | |
|---|---|---|
| *A61B 5/08* | (2006.01) | |
| *A61B 5/06* | (2006.01) | |
| *A61B 1/267* | (2006.01) | |
| *A61B 6/00* | (2006.01) | |
| *A61B 34/10* | (2016.01) | |

(52) U.S. Cl.
CPC .............. *A61B 5/06* (2013.01); *A61B 5/066* (2013.01); *A61B 1/267* (2013.01); *A61B 6/541* (2013.01); *A61B 2034/105* (2016.02)

(58) Field of Classification Search
CPC ....................................................... A61B 5/06
See application file for complete search history.

(56) References Cited

U.S. PATENT DOCUMENTS

| | | | |
|---|---|---|---|
| 5,480,422 A | 1/1996 | Ben-Haim | |
| 5,558,091 A | 9/1996 | Acker et al. | |
| 5,729,129 A | 3/1998 | Acker | |
| 5,752,513 A | 5/1998 | Acker et al. | |
| 5,928,248 A | 7/1999 | Acker | |
| 6,016,439 A | 1/2000 | Acker | |
| 6,147,480 A | 11/2000 | Osadchy et al. | |
| 6,161,032 A | 12/2000 | Acker | |
| 6,201,387 B1 | 3/2001 | Govari | |
| 6,203,493 B1 | 3/2001 | Ben-Haim | |
| 6,211,666 B1 | 4/2001 | Acker | |
| 6,233,476 B1 | 5/2001 | Strommer et al. | |
| 6,314,310 B1 | 11/2001 | Ben-Haim et al. | |
| 6,332,089 B1 | 12/2001 | Acker et al. | |
| 6,335,617 B1 | 1/2002 | Osadchy et al. | |
| 6,366,799 B1 | 4/2002 | Acker et al. | |
| 6,373,240 B1 | 4/2002 | Govari | |
| 6,380,732 B1 * | 4/2002 | Gilboa | 324/207.17 |
| 6,427,314 B1 | 8/2002 | Acker | |
| 6,453,190 B1 | 9/2002 | Acker et al. | |
| 6,484,118 B1 | 11/2002 | Govari | |
| 6,580,938 B1 | 6/2003 | Acker | |
| 6,591,129 B1 | 7/2003 | Ben-Haim et al. | |
| 6,618,612 B1 | 9/2003 | Acker et al. | |
| 6,650,927 B1 | 11/2003 | Keidar | |
| 6,690,963 B2 | 2/2004 | Ben-Haim et al. | |
| 6,788,967 B2 | 9/2004 | Ben-Haim et al. | |
| 6,995,729 B2 | 2/2006 | Govari et al. | |
| 7,197,354 B2 | 3/2007 | Sobe | |
| 7,236,567 B2 | 6/2007 | Sandkamp et al. | |
| 7,286,868 B2 | 10/2007 | Govari | |
| 7,301,332 B2 | 11/2007 | Govari et al. | |
| 7,321,228 B2 | 1/2008 | Govari | |
| 7,324,915 B2 | 1/2008 | Altmann et al. | |
| 7,343,195 B2 | 3/2008 | Strommer et al. | |
| 7,353,125 B2 | 4/2008 | Nieminen et al. | |
| 7,366,562 B2 | 4/2008 | Dukesherrer et al. | |
| 7,370,656 B2 | 5/2008 | Gleich et al. | |
| 7,373,271 B1 | 5/2008 | Schneider | |
| 7,386,339 B2 | 6/2008 | Strommer et al. | |
| 7,397,364 B2 | 7/2008 | Govari | |
| 2001/0031919 A1 | 10/2001 | Strommer et al. | |
| 2003/0086599 A1 | 5/2003 | Armato et al. | |
| 2004/0086161 A1 | 5/2004 | Sivaramakrishna | |
| 2004/0097804 A1 | 5/2004 | Sobe | |
| 2004/0097805 A1 | 5/2004 | Verard et al. | |
| 2004/0138548 A1 | 7/2004 | Strommer et al. | |
| 2004/0249267 A1 | 12/2004 | Gilboa | |
| 2005/0033149 A1 | 2/2005 | Strommer et al. | |
| 2005/0107688 A1 | 5/2005 | Strommer | |
| 2005/0197566 A1 | 9/2005 | Strommer et al. | |
| 2006/0058647 A1 | 3/2006 | Strommer et al. | |
| 2006/0064006 A1 | 3/2006 | Strommer et al. | |

(Continued)

FOREIGN PATENT DOCUMENTS

WO    WO 2006/095221 A2    9/2006

OTHER PUBLICATIONS

McLeish et al (IEEE transactions on Medical imaging (2002) vol. 21, 1142).*
(Merriam-Webster dictionary (1974) p. 629).*
Zaporozhan et al., Invest Radiol 2006;41:468-75.*
Deligianni et al., IEEE Trans Medical Imaging 2006;25:1462-71.*
Tsunashima et al., Int. J Radiat Oncol Biol Phys 2004;60;951-8.*
Koch et al. Int J Radiat Oncol Biol Phys 2004;1459-72.*
Cai et al. Phys Med Biol 2007;52:365-73.*
Davis, Med Engineer Phys 1999;21:619-23.*
Murthy et al. IEEE EMBS 2004.*
McClelland et al. Med Phys 2006;33:3348-58.*
Nehrke et al. Magn Reson Med 2005;54:1130-8.*
Manke et al. IEEE Transact Med Imag 2002;21:1132-41.*
Radiofrequency coil. Wikipedia 2004, retrieved 2016.*
WIPO, U.S. International Search Authority, International Search Report and Written Opinion dated Sep. 24, 2009 in International Patent Application No. PCT/IB2008/003728, 8 pages.
Shmarak, Itzhak, U.S. Appl. No. 10/986,567, specification and drawings as filed Nov. 10, 2004 (unpublished), assignee Mediguide Ltd., 84 pages.

(Continued)

*Primary Examiner* — Scott Long

(57) ABSTRACT

A method of accounting for the movement of the lungs during an endoscopic procedure such that a previously acquired image may be dynamically registered with a display showing the position of a locatable guide. After an initial image set is acquired, an area of interest is identified and the movement thereof due to breathing is mathematically modeled. Patient movement sensors are then used to provide information on the patient's breathing patterns. This information is entered into the mathematical model in order to update the registration between the image set and a display showing the position of the locatable guide.

9 Claims, 12 Drawing Sheets

(56) References Cited

U.S. PATENT DOCUMENTS

| | | |
|---|---|---|
| 2006/0074292 A1 | 4/2006 | Thomson et al. |
| 2006/0149134 A1* | 7/2006 | Soper et al. ............ 600/182 |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0287901 A1 | 12/2007 | Strommer et al. |
| 2008/0097187 A1 | 4/2008 | Gielen et al. |
| 2008/0132909 A1 | 6/2008 | Jascob et al. |
| 2008/0132911 A1 | 6/2008 | Sobe |
| 2008/0139915 A1 | 6/2008 | Dolan et al. |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |

OTHER PUBLICATIONS

European Search Report dated Jul. 10, 2013 from corresponding Euopean Application No. 08860538.1 (9 pgs.).
European Examination Report dated Apr. 21, 2016 for Application No. 08 860 538.1.

* cited by examiner

PATIENT BREATHING MODELING

RELATED APPLICATIONS

This application claims priority to U.S. Provisional Application Ser. No. 60/948,640 filed Jul. 9, 2007 entitled Patient Breathing Modeling; and U.S. Provisional Application Ser. No. 61/043,987 filed Apr. 10, 2008 entitled Patient Breathing Modeling, all of which are hereby incorporated by reference.

BACKGROUND OF THE INVENTION

The method of the present invention relates generally to the accurate registration of a detected sensor located in moving lungs to a static image of the lungs. The evolution of procedures using less-invasive scopes has resulted in the development of sensors that can be attached to end of an endoscope and used to determine the three-dimensional location and orientation of the end of the endoscope. Examples of such sensor technology is shown and described in various patents and patent publications including U.S. Pat. No. 6,188,355 to Gilboa, U.S. Pat. No. 6,380,732 to Gilboa, U.S. Pat. No. 6,593,884 to Gilboa et al., U.S. Pat. No. 6,615,155 to Gilboa, U.S. Pat. No. 6,833,814 to Gilboa et al., U.S. Pat. No. 6,947,788 to Gilboa et al., each of which is incorporated herein in its entirety. Additionally, there are many other technologies (laser technology, ultrasound technology, etc.) directed toward for locating a medical tool (catheter, endoscope, needle) inside the human lungs.

One problem that arises while using these localization methods is that, in order to provide information that is useful to a physician, a display must be used that shows a representation of the tool superimposed on an image of the lungs. If a static image of the lungs is used, the tool, which is moving with the lungs as the patient breathes, appears to float in and out of the airways in the preliminary, relatively static image. Accurately matching the position of the sensor in the lungs to an image of the lungs is achieved by "registration." Ideally, the desired result of registration would involve matching the tool representation to a real-time, dynamic image of the lungs. However, this would require constant exposure to X-ray radiation by both the patient and the medical staff during while performing the dynamic registration.

One approach at solving this problem is described in U.S. Pat. No. 7,117,026 to Shao et al., which is incorporated by reference herein in its entirety. Shao is directed to reconciling a dynamic, PET imaging data set with a static CT imaging data set. Shao accomplishes this by merely morphing (stretching or distorting) the image sets together. Doing so does not necessarily improve the accuracy of the real-time data being displayed because at least one of the data sets is being distorted. Rather, this approach merely makes the display appear to be more accurate. Moreover, PET requires prolonged exposure to radioactive imaging agents.

Another approach at solving this problem is described in U.S. Patent Publication No. 2003/0185346 to Vilsmeier. Vilsmeier is directed to avoiding costly CT scans by building a generic model of various areas of the body using a compilation of data from various patients, and then adapting that generic model to a specific patient. This idea certainly reduces costs and exposure to radiation, however it necessarily compromises image accuracy. Moreover, though the anatomy of the trachea and upper bronchial anatomy is very similar in most people, the lower bronchi become very patient-specific. It is in these lower bronchi where accurate information is most important. Finally, Vilsmeier does not address developing a dynamic model. Not only are the lower bronchi more patient-specific, they move more. So even if one where to use the Vilsmeier model to create a dynamic lung simulation, the lack of accuracy in the lower bronchi would not solve the problem the present invention addresses.

One reference that discusses the development of a generic model and begins to analyze the movement vectors for a breathing cycle is entitled "Development of a Dynamic Model for the Lung Lobes and Airway Tree in the NCAT Phantom" and is written by Garrity et al. This reference was published in 2002 as part of the Nuclear Science Symposium Conference Record, and appears in IEEE Vol. 3, pp. 1858-1862. This reference is incorporated herein in its entirety. It describes an algorithm that fills an empty outline of a simulated lung lobe with a virtual bronchial tree. The bronchial tree simulates movement due to breathing and cardiac rhythms. Because the model is completely simulated, it is useful for studying lung movement and the effects of tumor, but it would not have application during a procedure on an actual patient. Additionally, the reference discusses movement vectors within the lungs, but it does not find a mathematical relationship between these various vectors.

There is thus an identified need for a representation of the lungs that is more representative of a breathing patient's lungs than a static, previously acquired image, but does not result in an increased exposure to radiation.

SUMMARY OF THE INVENTION

The method of the present invention provides a representative modeling of the human lungs, based on statistical anatomical data, which can be tailored to the size and shape of an individual patient. The method of the present invention also utilizes a compilation of statistical anatomical data regarding lung movement in order to predict the movement of an individual patient's lungs during the breathing cycle.

Breathing causes the lungs to move cyclically. The movement varies by amplitude and direction during the breathing cycle from 5 mm to 30 mm depending on such breathing characteristics as patient size, age, altitude, health, etc. In order to reduce the deviation this movement causes between a living patient and a static image, lung movement is modeled. Dynamic modeling, according to the present invention, is based on a comparison of multiple CT data sets.

In one embodiment of the present invention, one or more static images, such as a CT data set, may be "brought to life" by applying a mathematical model that predicts how a given point in the lungs will move during the breathing cycle, based on a large sample of statistical data. The mathematical model is tied to one or more external position sensors on the patient's chest. Hence, by monitoring the external sensor(s), and applying the mathematical movement model, an instantaneous position of a given point in the lungs can be predicted. The patient's breathing cycle and its parameters may alternatively be monitored using internal sensors, or other devices such as spirometry devices, for example.

In another embodiment, each data set will preferably include at least one exhale scan and one inhale CT scan, acquired while the patient is holding an exhaled state or inhaled state, respectively. These scans will then be used as the extreme positions of the patient's breathing cycle.

The aforementioned mathematical movement model is then used to fill in the lung positions between the inhalation and exhalation points acquired by the CT scans of the actual patient. Additionally, any scans taken of the patient's lungs in intermediate breathing positions could also be added to the dynamic modeling set. Such acquired actual position data may be used to validate or modify the mathematical model as appropriate.

Alternatively, instead of matching the patient's characteristics to previously acquired CT scans of one or more other patients, the path a given point in a lung travels between inhalation and exhalation can be described mathematically and stored in a computer. The mathematical equations of the movement can be tied to one or more marker positions, so as the patient breathes, the computer may calculate the corresponding position of the point based on the position of the one or more markers. The computer can then implement the mathematical equations stored for a plurality of points to either create a dynamic representation of the lungs and present this to the user via a display, or synchronize this movement with the real-time movement of the LG and present the LG as though it were not moving cyclically, just advancing and turning according to its manipulation by the user. In other words, the computer can use the plurality of mathematical equations as a filter, applied to the graphic display of the LG.

Example 1

Constantly measuring the point at which a patient is in the breathing cycle allows a corresponding CT scan, which is closer to the actual position to the location of the sensor to be displayed over the sensor image.

Example 2

The measured location of the tool can be corrected using the patient breathing model. In this way the tool may be localized more correctly inside the CT volume. And therefore any geometric model derived from the CT volume can be more accurately represented relative to the tool inside the body.

Example 3

Using a well known technique called image warping, the CT Volume can be changed dynamically using the patient breathing model and according to the monitored phase of breathing cycle. This can be used to display augmented reality images to perform the simulation of dynamic X-Ray modalities such as fluoroscopy, dynamic CT, etc., to simulate the patient physiology synchronized to the actual patient, study the tissue movement relative to the inserted tools, and for other purposes as well.

DETAILED DESCRIPTION OF THE INVENTION

Figure 1:
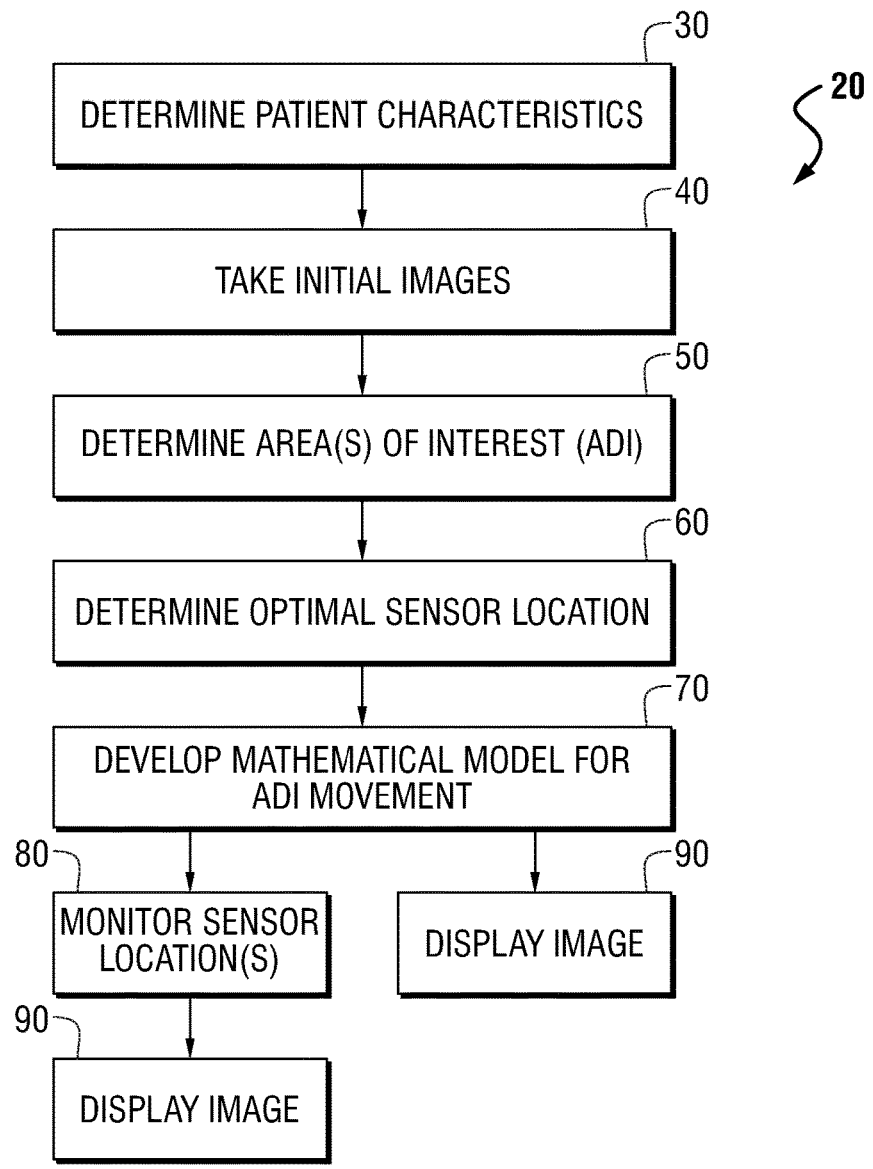
FIG. 1 is a flowchart of one embodiment of the method of the present invention.

Referring now to the figures and first to FIG. 1, there is shown a flowchart that illustrates one embodiment 20 of the method of the present invention.

At 30 the patient characteristics are measured or determined. "Patient characteristics" is a term defined herein as any attribute of the patient that will influence the position of his or her lungs during any given point in the breathing cycle. Patient characteristics include, but are not limited to patient size (lung size), lung shape, lung health, altitude, patient age, diaphragm size, and diaphragm health. Though altitude is not intrinsic to any given patient, the elevation at which a patient is breathing impacts the depth and/or the frequency of the breaths taken during the breathing cycle. Lung health relates to the lung capacity of a given patient and includes such factors as whether the patient smokes, whether the patient has an increased lung capacity due to athletic training, whether the patient has a condition such as cystic fibrosis, etc. One skilled in the art will realize that some patient characteristics are more determinative of lung position than others and that it may only be feasible to factor a few of the listed characteristics into the matching process described below. Moreover, which factors are most determinative will likely vary by patient. Many of the characteristics can be measured using a CT scan performed prior to the procedure.

At 40 the patient is imaged using any imaging modality that shows the lungs or desired target area. Most likely, CT imaging will be used. The CT imaging may be high definition CT and preferably a first image set is taken with the lungs full of air and a second image set is taken after the patient has fully exhaled. However, it is envisioned that a single CT image set may be used if there is accurate data regarding how full the lungs are when the image is taken.

At 50 the images taken at 40 are reviewed and at least one area of interest (hereinafter "AOI") is identified. Identifying an AOI will allow the focus to remain on applicable areas of the lungs and reduce the number of computations that have to be made in later steps.

At 60 it is determined where the patient position sensors should be placed. The patient position sensors are sensors on the chest, sensors in the lungs, or a device such as a spirometry device, that are used to measure the positions of key points on the patient's body in order to determine where the patient is in the breathing cycle. The data from these sensors are not only used as an entering argument for the upcoming mathematical modeling step 70, but also to monitor the physical location of the patient in order to register a real-time image (such as that acquired to show the position of the locatable guide) to the CT scan image(s).

At 70 a mathematical model is developed to describe the movement at one or more points in the AOI(s) during the breathing cycle. The mathematical model uses data from the patient position sensors as entering arguments and the result of the solved algorithm is a three dimensional position of the point in question. Selecting more points in a given AOI will result in a better registration between a display of the locatable guide (LG) and the CT scan taken at 40. The mathematical algorithm used to develop the model may be obtained by collecting data on a number of subjects in a study and relating the movement of given points to the point in the breathing cycle in which the positions were acquired. Alternatively, the mathematical algorithm may be developed using computer simulated models, such as those described in the aforementioned Garrity et al. reference. Examples of algorithms developed for the present invention and proven useful through experimentation are described below.

At 80 the procedure begins on the patient. The patient movement sensors are placed on or in the patient. The physician intubates the patient and the LG is inserted and tracked. The CT scan from 40 is displayed and registered to the superimposed LG display.

As the LG is being inserted, the location(s) of the patient location sensors are constantly monitored and entered into the algorithm to provide three dimensional location data on the AOI(s). This information is then used at 90 to ensure that the display is modified such that the LG display maintains an accurate registration with the CT scan, despite the movement of the lungs, which cause the LG to move.

There are at least three ways at 90 in which the data acquired from 80 can be used to improve the registration between the LG display and the CT scan. These three examples are not to be considered exclusive, as one skilled in the art will see the usefulness of the data acquired at 80 and realize other ways to apply the data at 90 or subsequent steps.

Example 1

If multiple CT scans were acquired at 40, the data acquired at 80 may be used to determine which CT scan most accurately depicts the configuration of the lungs and can thus be superimposed onto the LG display.

Example 2

The measured location of the LG can be corrected using the data acquired at 80. Rather than displaying the real-time data acquired by the LG system, which represents the position of the LG in relation to a magnetic field filling the AOI, the real-time data is manipulated so the LG appears in the correct location on the CT scan, which may be static or dynamic. In this way the tool may be localized more correctly inside the CT volume. The geometric model derived from the CT volume can thus be more accurately represented relative to the tool inside the body.

Example 3

Using a well-known technique called image warping, the CT Volume can be changed dynamically using the data acquired at 80 and according to the monitored phase of breathing cycle. This can be used to display augmented images to perform the simulation of dynamic X-Ray modalities such as fluoroscopy, dynamic CT, etc., to simulate the patient physiology synchronized to the actual patient, study the tissue movement relative to the inserted tools, and for other purposes as well.

Figure 2:
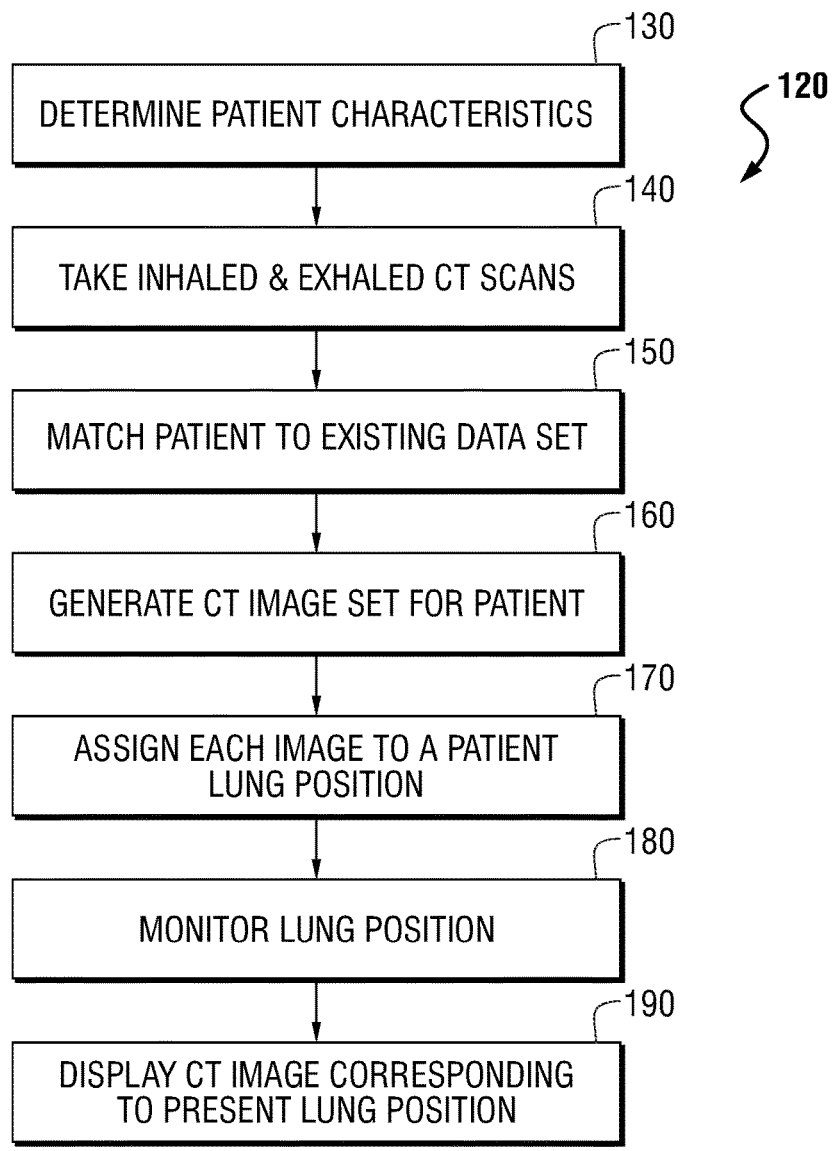
FIG. 2 is a flowchart of a second embodiment of the method of the present invention; and, FIGS. 3-12 are graphs and charts showing the data results of experiments conducted on seven patients using the methods of the present invention.

Referring now to FIG. 2, there is shown a flowchart that illustrates another embodiment 120 of the method of the present invention.

At 130 the patient characteristics are measured or determined. "Patient characteristics" is a term defined herein as any attribute of the patient that will influence the position of his or her lungs during any given point in the breathing cycle. Patient characteristics include, but are not limited to patient size (lung size), lung shape, lung health, altitude, patient age, diaphragm size, and diaphragm health. Though altitude is not intrinsic to any given patient, the elevation at which a patient is breathing impacts the depth and/or the frequency of the breaths taken during the breathing cycle. Lung health relates to the lung capacity of a given patient and includes such factors as whether the patient smokes, whether the patient has an increased lung capacity due to athletic training, whether the patient has a condition such as cystic fibrosis, etc. One skilled in the art will realize that some patient characteristics are more determinative of lung position than others and that it may only be feasible to factor a few of the listed characteristics into the matching process described below. Moreover, which factors are most determinative will likely vary by patient. Many of the characteristics can be measured using a CT scan performed prior to the procedure.

At 140 the patient is imaged using any imaging modality that shows the lungs or desired target area. Most likely, CT imaging will be used. Preferably a first image set is taken with the lungs full of air and a second image set is taken after the patient has fully exhaled.

At 150 the patient is matched to an archived data set taken from a data library. It is desirable to find an archived data set that matches the patient's breathing cycle as closely as possible. In order to match a data set to the patient, the patient characteristics are used as matching criteria. The specific characteristics that are used, and the number of different characteristics that are used, are largely dependent on the size of the data library. However, if the patient has any distinguishing lung traits, such as a significantly reduced capacity due to smoking, they should be given more weight than other, less-distinguishing traits when looking for a matching data set.

Alternatively, the inhaled and exhaled positions recorded and measured using CT scans could be used as the entering arguments for matching the patient to a data set. If the inhaled and exhaled positions are closely matched to a data set, it will be likely that the intermediate points between inhalation and exhalation will also match. However, considerations like patient size should still be considered to ensure that the lung geometries are also matched.

At 160 a CT image set for the patient is generated. The closely-matched data set is either used alone, or if inhalation and exhalation CT scans have been taken, they are added to the data set to improve the degree to which the data set is matched to the actual patient geometry.

At 170 each image of the image set is assigned to a lung position, as measured by external or internal means. Because each of the images will be displayed during the procedure at different times during the breathing cycle, it is necessary to determine, in advance, when each image will be cued for display. There are at least two ways in which this may be done. First, the positions of sensors, such as external sensors placed on the patient's chest, may be monitored throughout the breathing cycle. Each image may be examined to determine a position of the lungs that is most closely matched to that particular image. When the external sensors indicate a particular lung position, the image will be changed to the most closely matched image. Second, an average breathing cycle may be measured to determine the inhaling period (defined herein as the amount of time between inhalation and exhalation) and the exhaling period (defined herein as the amount of time between exhalation and inhalation). At the beginning of the inhaling period it will be known to display the inhalation image taken at 150. At the exhalation point, it will be known to display the exhalation image taken at 150. The measured periods may be divided by the number of intermediate images in the data set to determine an interval time. The images will then be changed each interval.

At 180 the actual procedure begins. During the procedure, the lung position is monitored. If the first method at 170 was used, sensors on the chest, sensors in the lungs, or a device such as a spirometry device is used to determine when the images shall be displayed at 190 to most accurately represent the actual lungs. If the second method at 170 was used, the breathing cycle will be monitored using any of the aforementioned sensors or devices, to update the average inhaling and exhaling periods of the breathing cycle. At 190, the images will be changed according to the constantly-updated intervals.

One skilled in the art will realize that the second method at 160 avoids the process of examining each individual image of the data set to assign it to a point in the breathing cycle. However, one skilled in the art will also see the potentially improved accuracy of the first method. Because an unconscious patient does not breathe at a constant depth, the inhalation points and exhalation points will vary during each breathing cycle. If the first method is used and the lung positions are monitored to determine which image to display at 190, during times of shallow breathing, the inhalation and exhalation scans may never be displayed. This is because during times of shallow breathing, the sensors will never measure a lung position that triggers the display of the scans taken at 140. However, if the second method is used, the extremes are shown each cycle. The only variance will be the frequency of the image changes.

In order to combine the advantages of first and second methods, one embodiment of step 170 maintains a constant image interval during shallow breaths but ends the progression of images shown from exhalation point when it is determined that the patient is no longer inhaling. In other words, it is assumed that no matter how shallow the breaths being taken are, the patient is still achieving a full exhalation. Shallow breaths mean the patient is not achieving a full inhalation. Thus, images are shown at a regular interval until the patient begins to exhale. Then, the images are shown in reverse order at the exhalation interval.

Algorithms and Experimental Results

Data Acquisition

An experiment was conducted that began with the acquisition of CT images of patients in two respiratory states: inhalation and exhalation. A database of patients was divided into three categories according to breathing amplitude (normal, moderate, extreme). Only patients with moderate (full inhalation, normal exhalation) amplitude breathing were used for the study.

For each patient about 200 pairs of points (landmarks) were marked on both exhalation and inhalations CT images. The anatomical points were marked on airway bifurcations or on blood vessels bifurcations for the peripheral areas where airway bifurcations were hardly to identify. Each pair of matching points represents a breathing vector at that specific anatomic location. Landmark locations were chosen to be uniformly distributed throughout the lung volume.

$T: R^3 \rightarrow R^3$ Transformation Method

Local tissue deformations can be learned by analyzing the displacements of each landmark point. The missing data between the displacements of each landmark point can be interpolated.

Non-rigid registration techniques were used in order to get marked landmark points to smoothly transform from one state to another. The methods, functions and kernels are chosen according to the stability of the transformation and robustness to possible outliers. The transformation techniques used include polynomials, basis functions, and splines.

Modeling can be performed for all landmarks to attain a global lung deformation function that can be used for global calculations. It is also possible to divide the lungs to smaller sub-parts that can be modeled separately while simplifying the needed transformation. For example, analyzing the left and right sides of the lungs separately yielded good results.

The methods of the present invention allow describing lung tissue deformations during breathing cycles using a low number of degrees of freedom with an acceptable level of inaccuracy. Hence, the transformation can be produced or reproduced using a small number of control points (internal and/or external) with locations sampled in real time.

The accuracy of the model is affected by the number of degrees of freedom of the transformation. However, overfitting the model to the data can make the model less robust. Approaching high transformation precision values on the landmarks themselves (less then 1 mm) requires the use of complicated solutions that can behave poorly on the volumes between landmarks and are, therefore, less suitable for modeling.

Though an entire breathing vector set can be used as input data for fitting algorithm, the vectors may be divided according to anatomical regions, such as left lung and right lung, for example.

Linear transformation models can be extended to non-linear transformation models. For second order polynomial transformation:

$$T(x, y, z,) = \begin{pmatrix} x' \\ y' \\ z' \\ 1 \end{pmatrix} = \begin{pmatrix} a_{00} & \Lambda & a_{08} & a_{09} \\ a_{10} & \Lambda & a_{18} & a_{19} \\ a_{20} & \Lambda & a_{28} & a_{29} \\ 0 & \Lambda & 0 & 1 \end{pmatrix} \begin{pmatrix} x^2 \\ y^2 \\ M \\ 1 \end{pmatrix}$$

A polynomial fit is a specific type of linear multiple regression.

In order to build a polynomial transformation between the inhalation and exhalation breathing phases, the available pairs of points are used. It is assumed that the points are distributed uniformly throughout the lungs and represent the global anatomical tissue displacement during the respiratory cycle.

Let U and V denote coordinates matrix of size 4×N for points of two states, inhalation and exhalation respectively:

$$U = (\vec{u}_1, \vec{u}_2, \ldots \vec{u}_N)$$

$$V = (\vec{v}_1, \vec{v}_2, \ldots \vec{v}_N)$$

For N pairs of points:

$$V = \begin{pmatrix} x'_1 & x'_2 & \Lambda & x'_N \\ y'_1 & y'_2 & \Lambda & y'_N \\ z'_1 & z'_2 & \Lambda & z'_N \\ 1 & 1 & \Lambda & 1 \end{pmatrix} = \begin{pmatrix} a_{00} & \Lambda & a_{08} & a_{09} \\ a_{10} & \Lambda & a_{18} & a_{19} \\ a_{20} & \Lambda & a_{28} & a_{29} \\ 0 & \Lambda & 0 & 1 \end{pmatrix} \begin{pmatrix} x_1^2 & x_2^2 & \Lambda & x_N^2 \\ y_1^2 & y_2^2 & \Lambda & y_N^2 \\ M & M & & M \\ 1 & 1 & \Lambda & 1 \end{pmatrix} = A\tilde{U}$$

where $$\tilde{U} = f(U) = \left( f(\vec{u}_1), f(\vec{u}_2), \ldots, f(\vec{u}_N) \right)$$

is the function that transforms each column vector of U containing x, y, z to a column vector of higher dimension. In case of a second degree polynomial, the 3D vector is transformed to 10D space by:

$$(x, y, z) \xrightarrow{f} (x^2, y^2, z^2, xy, xz, yz, x, y, z, 1)$$

The minimum number of point pairs needed for identification of the transformation is determined by the number of DOFs (degrees of freedom) for an output space of function f. Thus, for a second degree polynomial, just 10 point pairs (or breathing vectors) are required. For a third degree polynomial, a minimum of 20 point pairs are required respectively.

The mean error is calculated for all available points by:

$$\varepsilon = A\tilde{U} - V$$

$$m = \frac{1}{N}\sum_{i}^{N} \|\varepsilon_i\|_2$$

Deriving the Breathing Model

It is possible to calculate a polynomial transformation for each available dataset (patient) given a sufficient number of matched pairs of points representing exhalation and inhalation states. In order to assess the similarity between breathing models for different patients, the 3D vector fields should be compared. Due to the inherent variability of different patients, it is difficult to apply a breathing model of one patient directly to another patient. Nevertheless, there is an assumption that two breathing models can be matched together applying some simple transformation that can convert from one model to another:

$$T_{simple}(W) = S \cdot g(W)$$

where the g( ) transforms each vector to higher dimensional space and S is the appropriate coefficient matrix.

In order to minimize the number of degrees of freedom, it is assumed that the unknown transformation is a linear transformation (affine or perspective). Then the function g( ) performs the conversion into homogeneous coordinates. Therefore S is of size 4×4.

When looking for simple transformation the cost function can be defined:

$$\varepsilon = A \cdot f(S \cdot U) - S \cdot V$$

$$F = \frac{1}{N}\sum_{i}^{N} \|\varepsilon_i\|_2$$

$$S_{best} = \underset{S_{4\times 4}}{\operatorname{argmin}}(F)$$

This optimization problem is solved using Nelder-Mead method or the Simplex Search method. The method uses the concept of a Simplex, which is a polytope (generalization to any dimension of polygon) of N+1 vertex in N dimensions; a line segment on a line, a triangle on a plane, a tetrahedron in three-dimensional space and so forth. The method approximately finds a locally optimal solution to a problem with N variables when the objective function varies smoothly.

The search for the global minimum is performed as a part of the optimization task on the function F, defined above, in multi-dimensional space, which has 16 dimensions in this case.

The resulting $S_{best}$ is used to fit the known polynomial function to other patient with undefined breathing model.

Grid Method

Assuming elastic properties of lung tissue, deformation at any given point may be evaluated by close breathing vectors.

Initial breathing vectors were used for calculating new breathing vectors located at the nodes of 3D grid.

The described procedure was applied for 4 different patients after CT volume normalization and registration. The final 3D vector field was generated by averaging results of all patients.

For each grid vertex the integration is performed over defined volume space around (using defined kernel function). The integration boundaries can be 3D cube of size N or sphere with radius N.

Anatomical Points Method

The respiratory motion can also be described by means of modeling the "skeletal" motion of the lungs. A skeletal tree of the lungs is produced by representing the bifurcations of the airways as nodes and then connecting the nodes to form a skeleton of the airways.

Skeletal trees are generated for two breathing states of the same patient. Then the trees are combined together in order to identify the changes that are modeled later by measuring the relative angles at the nodes.

Skeletal trees from different individuals can be further analyzed by comparing the behavior of corresponding nodes from each patient.

The available data set has been divided to training and testing sets. The model parameters have been estimated by the training set and verified with the testing set proving the feasibility of the method.

Results

Transformation method: tissue deformations of the entire lung were modeled using smooth vector function with an average fit error of about 2 mm.

Grid method: 3 patients were used for building the model and 1 patient for verification. After applying cross validation, the average error was about 4 mm.

Breathing vectors for patients with normal breathing intensity was 1-2 mm in the central lung regions and 10-15 mm at the periphery (diaphragm).

Interpolation Results

The general breathing models that were obtained using the aforementioned technique were verified using cross-reference method. The model is derived from each of the available patients and then used for modeling breathing for other available patients, including one used for model generation in order to have a comparative lower limit error estimation.

Seven patients participated in the study. The following tables summarize the mean errors and standard deviations when applying the breathing model derived from the patient on the row to each of the patients from the columns.

Mean Errors:

| | Mean errors | | | | | | |
|---|---|---|---|---|---|---|---|
| | Patient 1 | Patient 2 | Patient 3 | Patient 4 | Patient 5 | Patient 6 | Patient 7 |
| Patient 1 | *1.4441* | 30.3849 | 22.3949 | 9.579 | 6.7975 | 9.1251 | 17.5015 |
| Patient 2 | 8.0471 | *2.1803* | 26.975 | 7.3234 | 6.2768 | 6.2002 | 9.4439 |
| Patient 3 | 27.2102 | 31.8968 | *3.9853* | 12.5647 | 10.1514 | 18.2088 | 32.9139 |
| Patient 4 | 4.7568 | 5.1671 | 8.9472 | *3.4243* | 7.0903 | 5.7553 | 6.1695 |

-continued

Mean errors

|  | Patient 1 | Patient 2 | Patient 3 | Patient 4 | Patient 5 | Patient 6 | Patient 7 |
|---|---|---|---|---|---|---|---|
| Patient 5 | 57.6078 | 22.6204 | 21.88 | 13.0142 | *3.6763* | 24.7327 | 41.5406 |
| Patient 6 | 31.4134 | 15.3444 | 51.4794 | 14.9238 | 13.7905 | *4.1377* | 27.2752 |
| Patient 7 | 19.0761 | 6.8696 | 8.2957 | 12.2098 | 6.9798 | 10.0902 | *2.403* |

Standard Deviation Values:

Standard deviation values

|  | Patient 1 | Patient 2 | Patient 3 | Patient 4 | Patient 5 | Patient 6 | Patient 7 |
|---|---|---|---|---|---|---|---|
| Patient 1 | *0.8592* | 12.2057 | 4.9473 | 4.4579 | 2.5962 | 5.4156 | 9.8278 |
| Patient 2 | 4.701 | *1.6283* | 13.9169 | 4.2816 | 3.4003 | 3.5902 | 7.437 |
| Patient 3 | 15.7571 | 17.4782 | *3.2823* | 6.9061 | 5.8878 | 12.9119 | 16.6467 |
| Patient 4 | 2.7333 | 3.9613 | 4.9235 | *2.321* | 3.1751 | 4.0883 | 4.2487 |
| Patient 5 | 3.8712 | 13.2514 | 9.6508 | 5.0819 | *2.6654* | 11.5002 | 16.0817 |
| Patient 6 | 9.4778 | 7.577 | 14.7764 | 9.0923 | 7.0307 | *2.7028* | 10.835 |
| Patient 7 | 9.6453 | 5.2156 | 5.168 | 5.9022 | 4.2303 | 6.7865 | *1.3058* |

The italicized cells in the tables above determine the quality of self-error, when the same patient used both for model derivation and for error calculation. This number is expected to have the lowest value in the row and column.

The existence of acceptable values of above-mentioned function F means that respiratory motion can be modeled by known polynomial function in conjunction with some linear transformation given by a 4×4 sized matrix.

Figure 3:
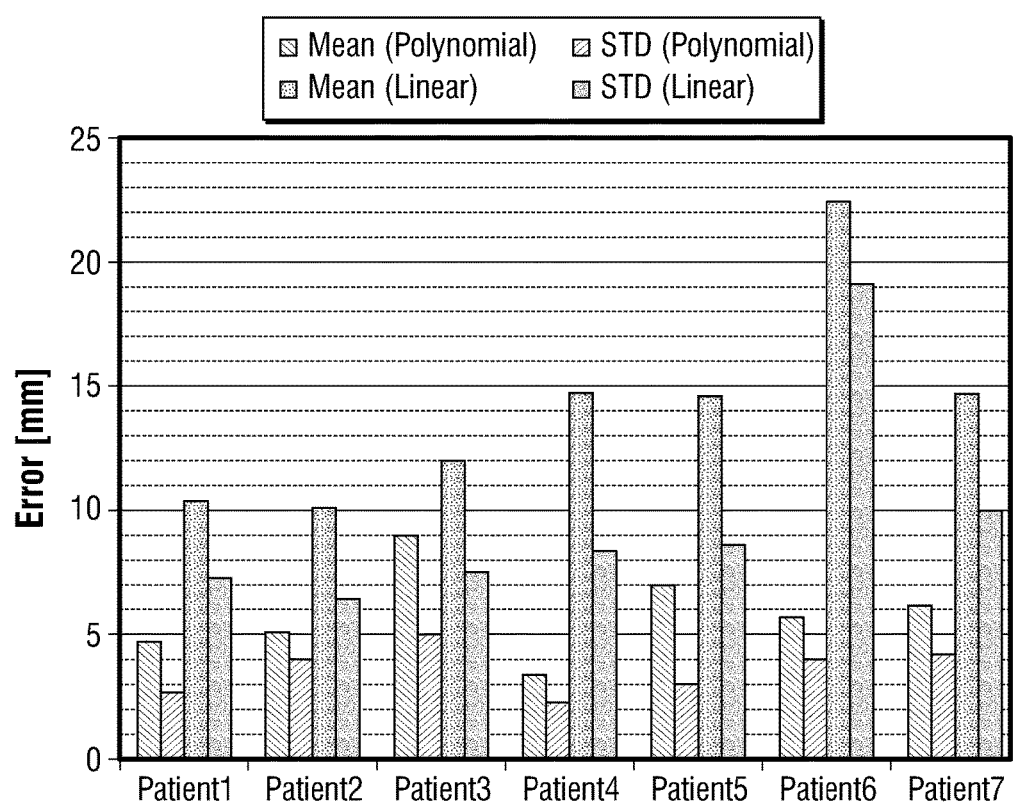
Figure 4A:
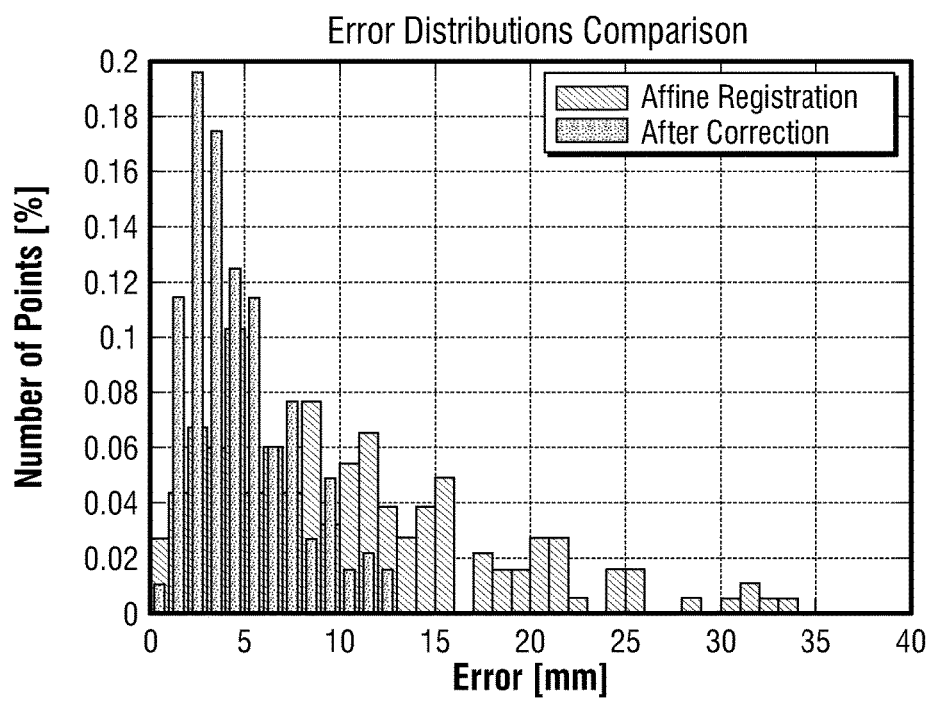
Figure 4B:
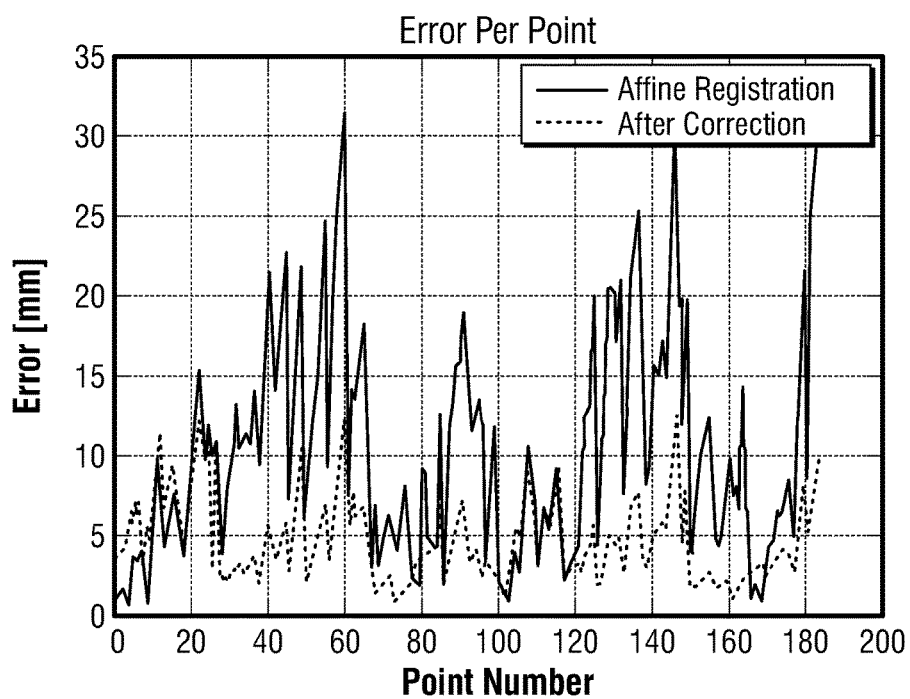
Figure 5A:
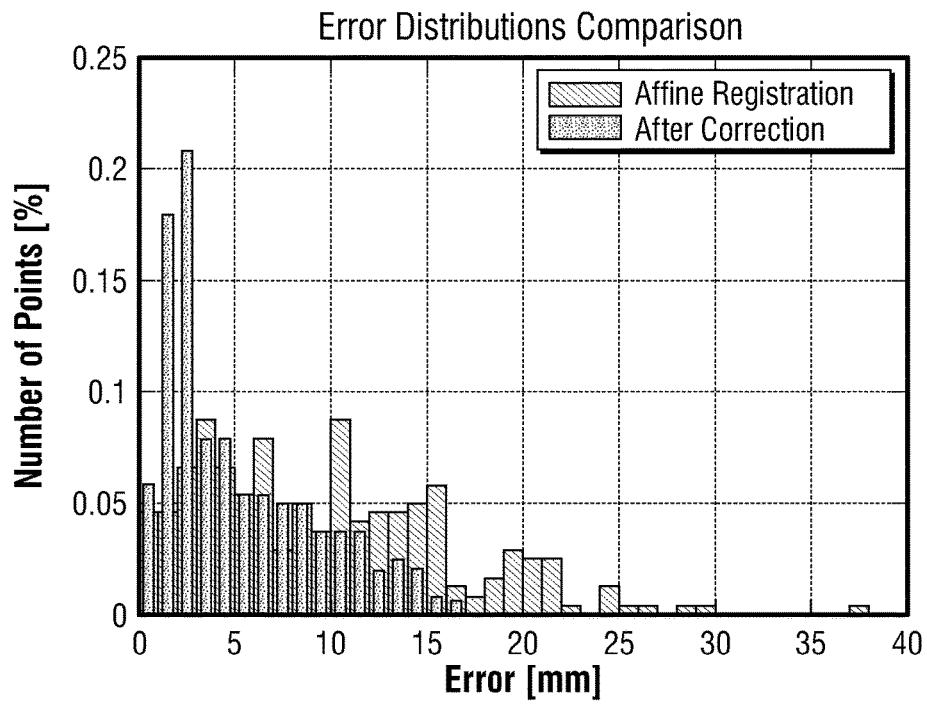
Figure 5B:
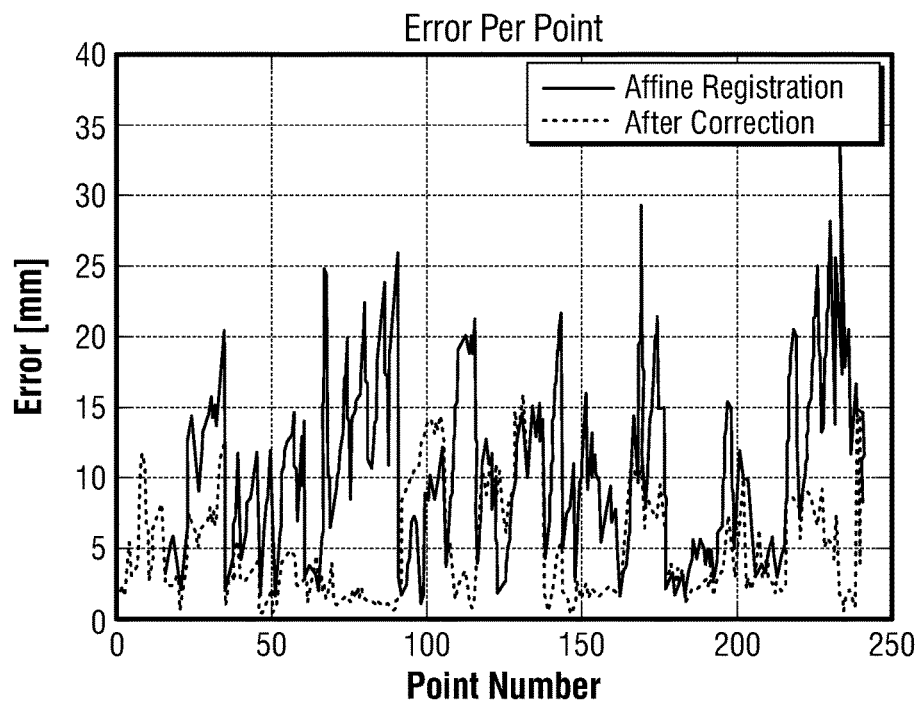
Figure 6A:
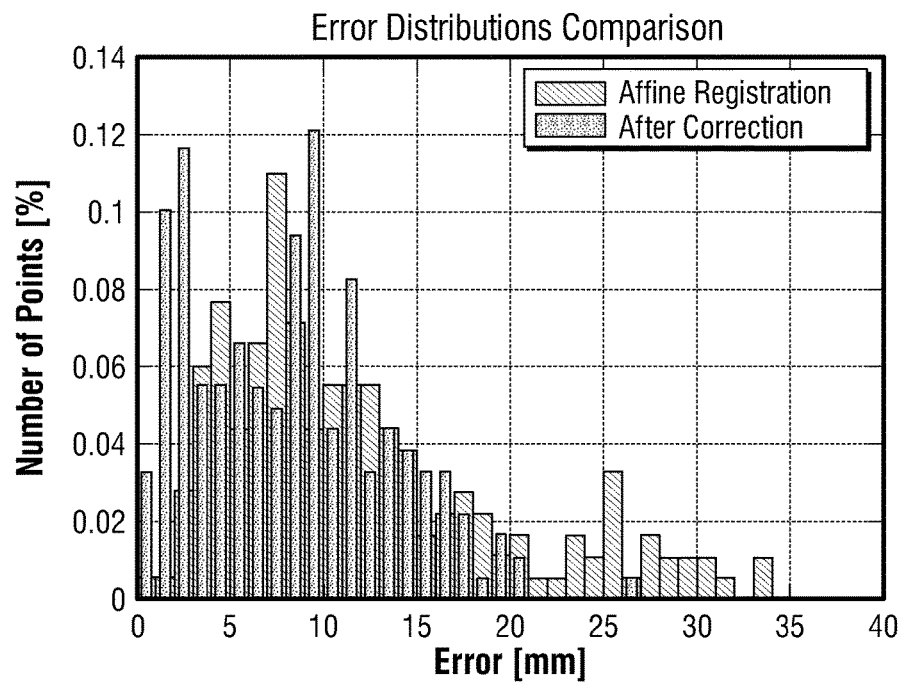
Figure 6B:
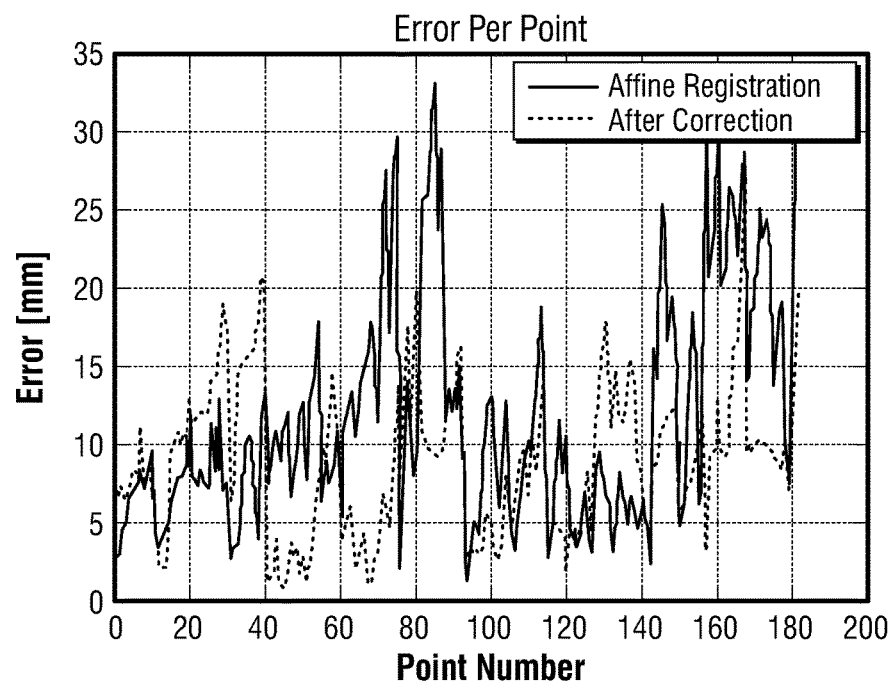
Figure 7A:
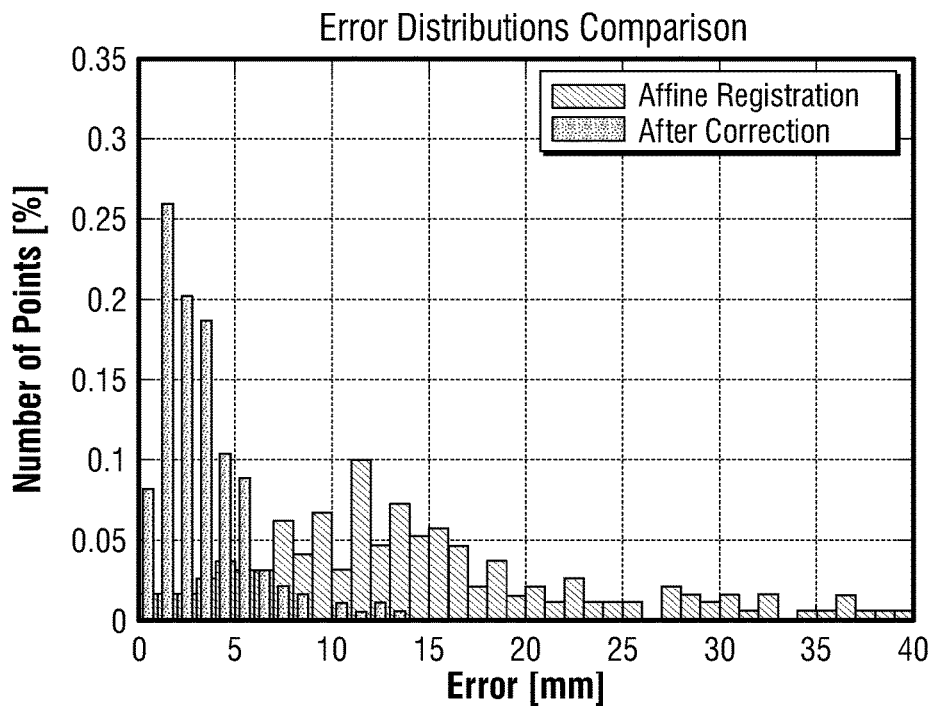
Figure 7B:
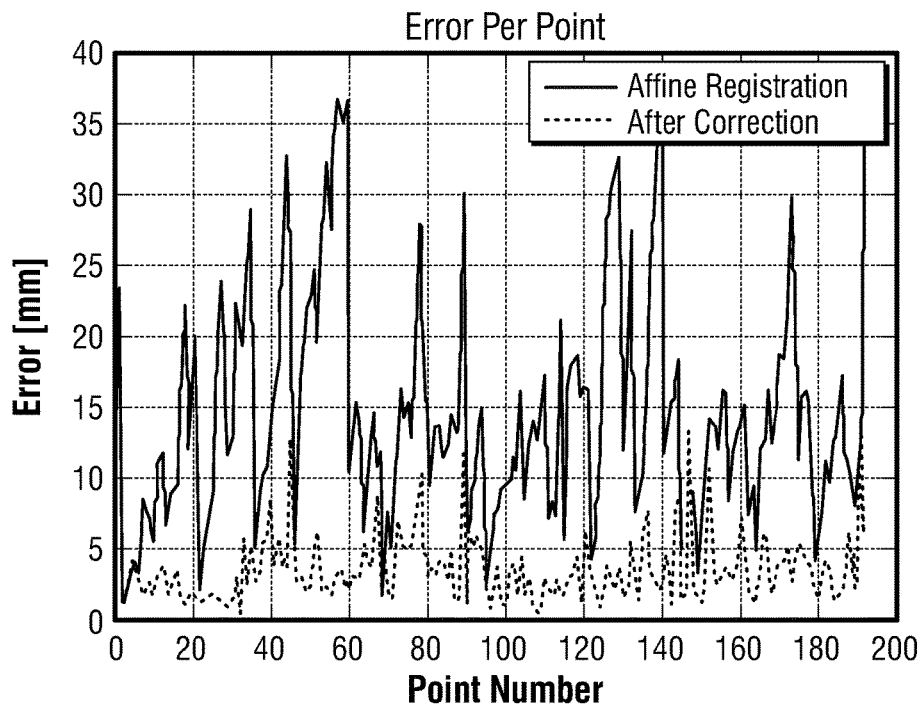
Figure 8A:
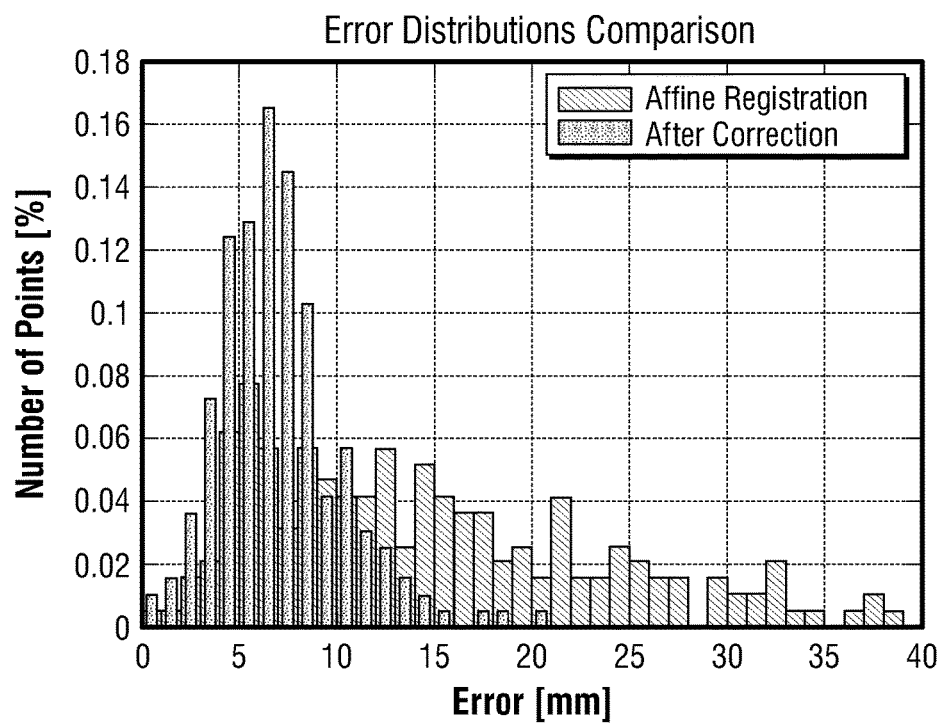
Figure 8B:
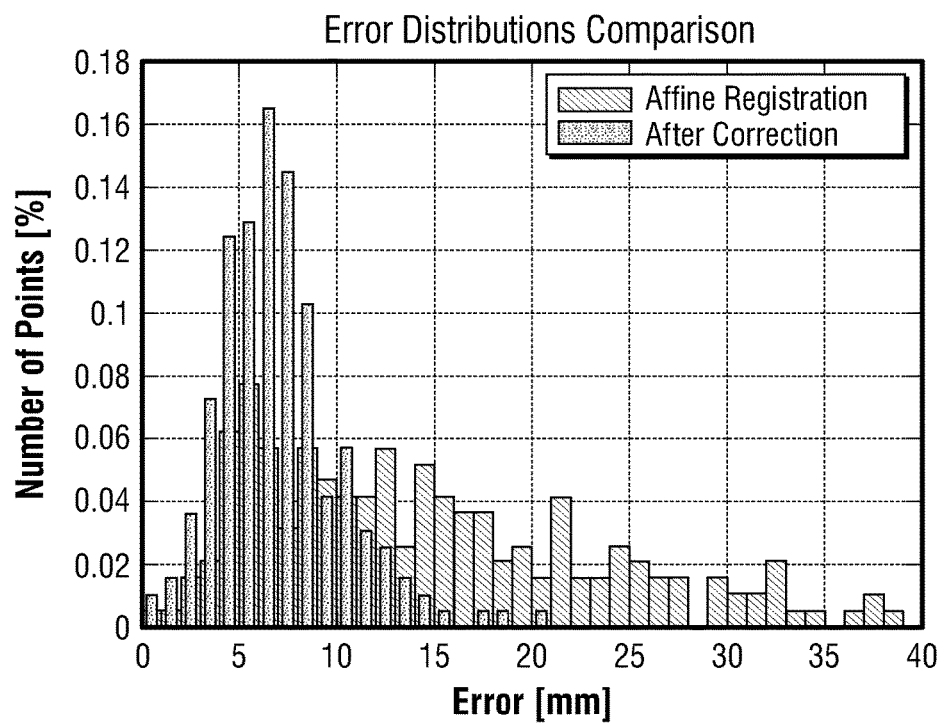
Figure 9A:
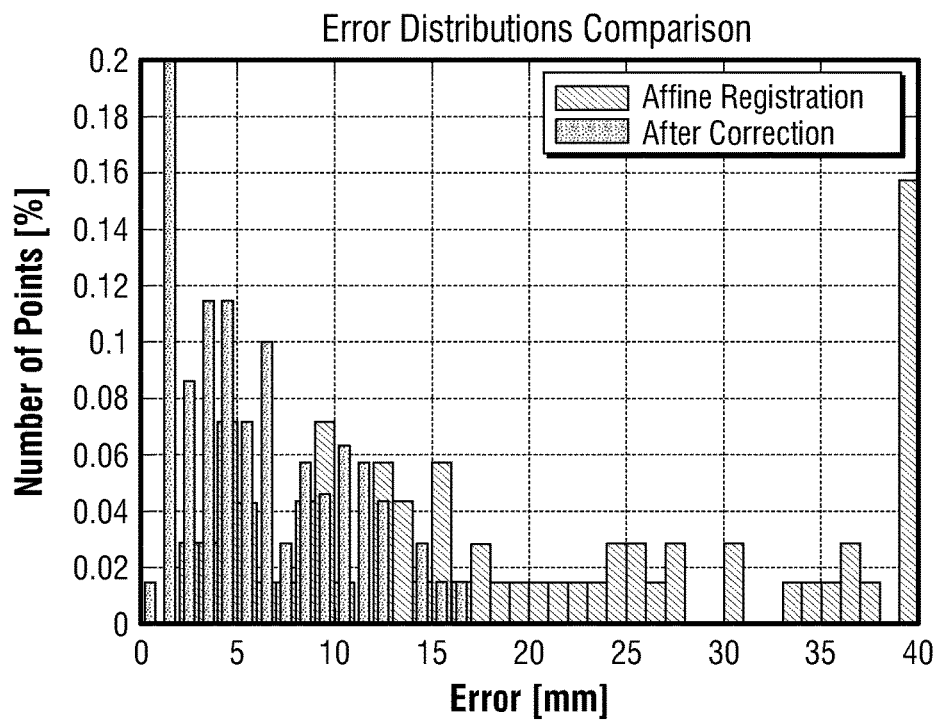
Figure 9B:
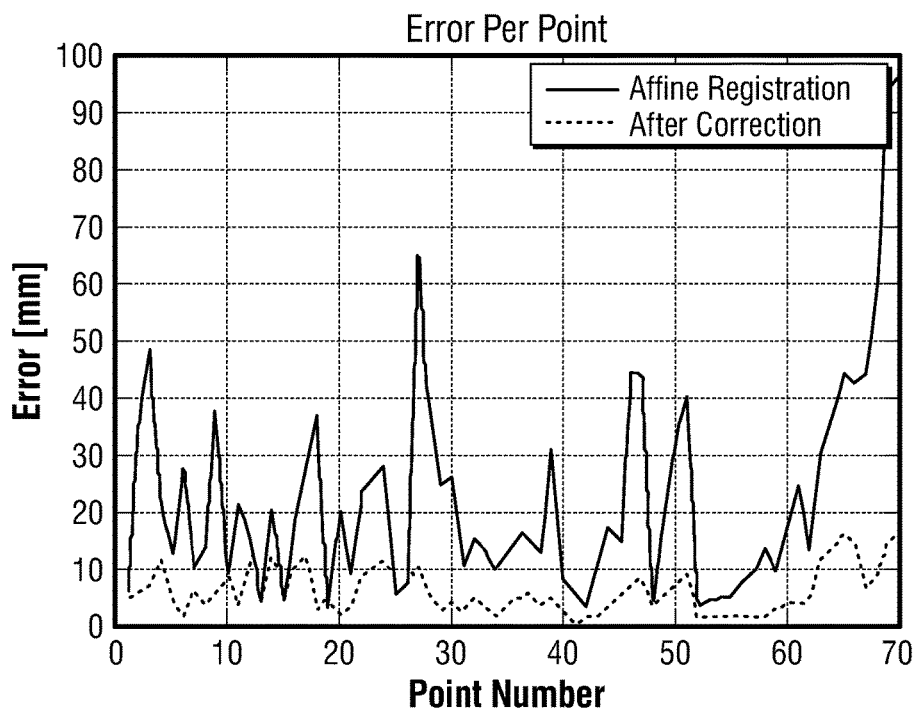
Figure 10A:
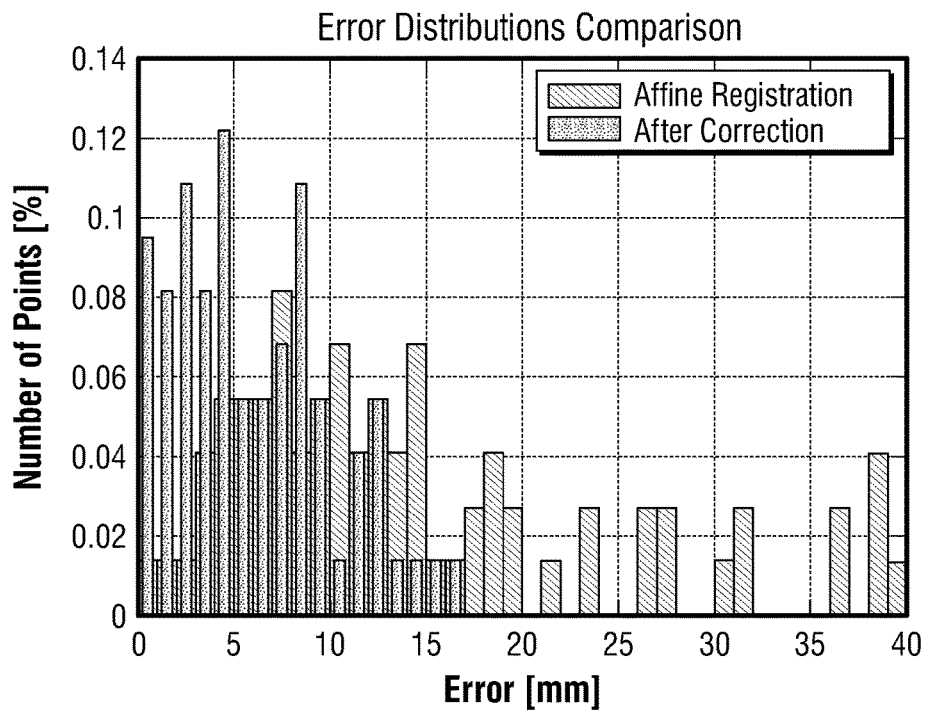
Figure 10B:
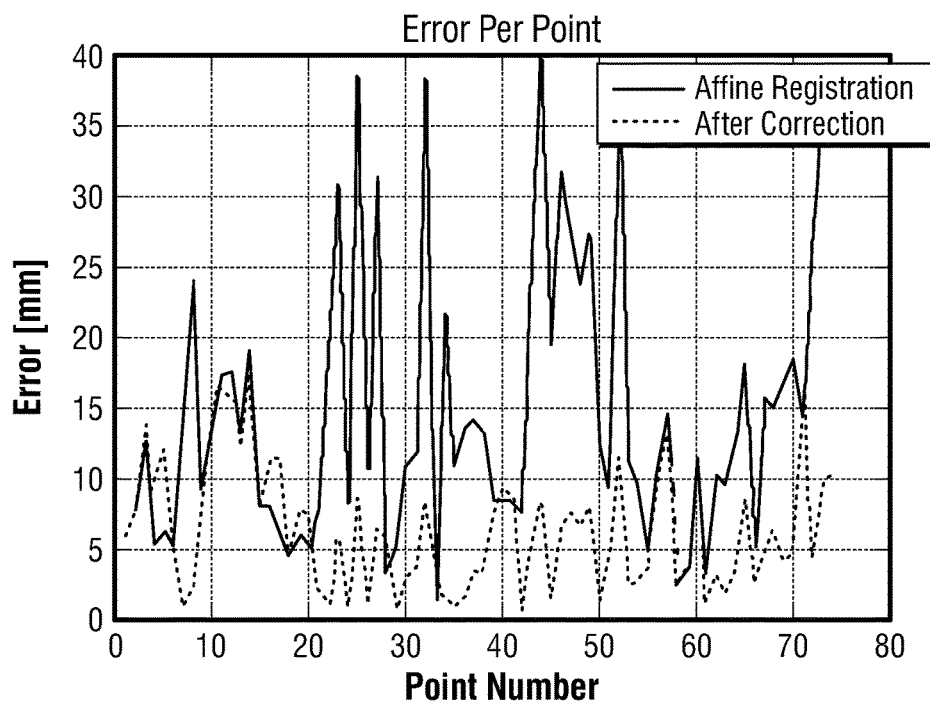

As charted in FIG. 3, it is observed that in the above patient-related CT dataset, the best results are achieved when using the breathing model generated from Patient4. The results of this polynomial approximation method can be compared to simple linear registration method using 7 registration points.

Mean and standard deviation for errors after simple affine registration using 7 registration points:

|  | Patient 1 | Patient 2 | Patient 3 | Patient 4 | Patient 5 | Patient 6 | Patient 7 |
|---|---|---|---|---|---|---|---|
| Mean | 10.4010 | 10.1197 | 11.9469 | 14.7198 | 14.5926 | 22.4039 | 14.7366 |
| Std | 7.2987 | 6.4501 | 7.5849 | 8.4310 | 8.6562 | 19.1004 | 10.0350 |

The above graph shows that approximation based on polynomial interpolation achieves significantly more accurate results than regular rigid registration. Graphs showing the breathing error distributions for each individual patient are provided as FIGS. 4-10:

Patient1: See FIGS. 4a and 4b.
Patient2: See FIGS. 5a and 5b.
Patient3: See FIGS. 6a and 6b.
Patient4: See FIGS. 7a and 7b.
Patient5: See FIGS. 8a and 8b.
Patient6: See FIGS. 9a and 9b.
Patient7: See FIGS. 10a and 10b.

It is drawn from the graphs in FIGS. 4-10 that breathing models obtained using the aforementioned technique were able to significantly reduce the errors (or divergence) caused by inhalation exhalation breathing states difference.

Generalization Analysis for Second Order Polynomial

It is proven that the generalization property has a significant effect on the registration error of volumes around the registration landmark points.

Figure 11:
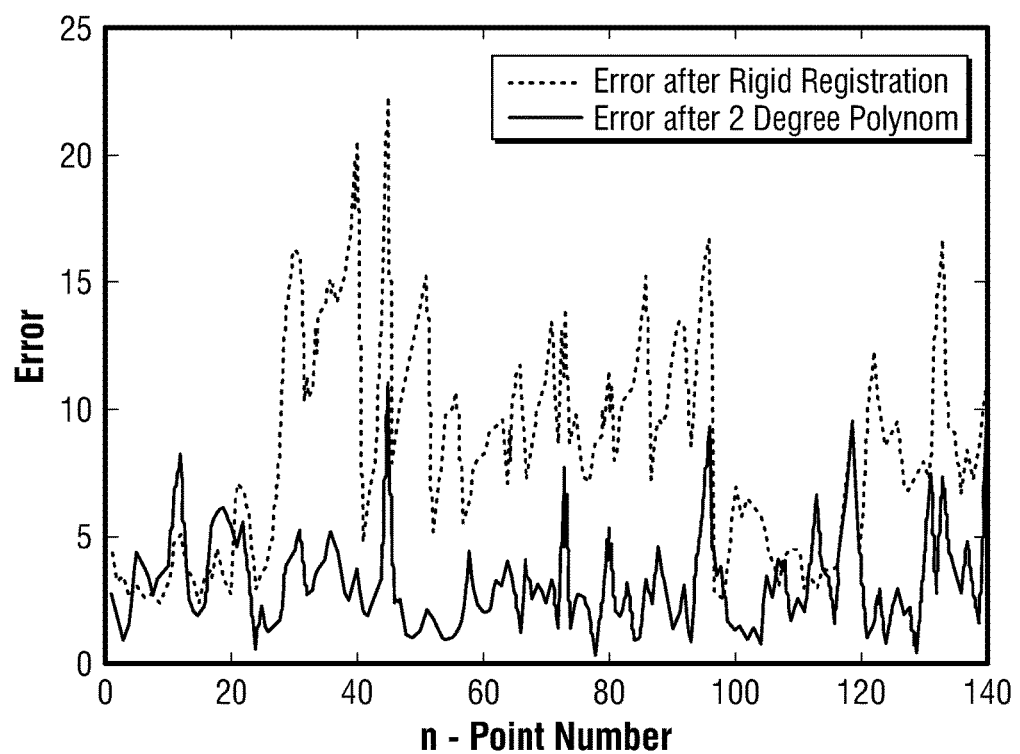

The graph of FIG. 11 shows the comparison of registration error between rigid and polynomial-based transformations. Note that each value shown on the graph corresponds to the specific pair that did not participate in registration data set. This way the results are not biased by the transformation. The FIG. 11 graph is based on left side lung registration.

Compare the mean values of 8.3 mm after rigid registration to 3.2 mm after polynomial based registration.

Degree of Polynomial

Figure 12:
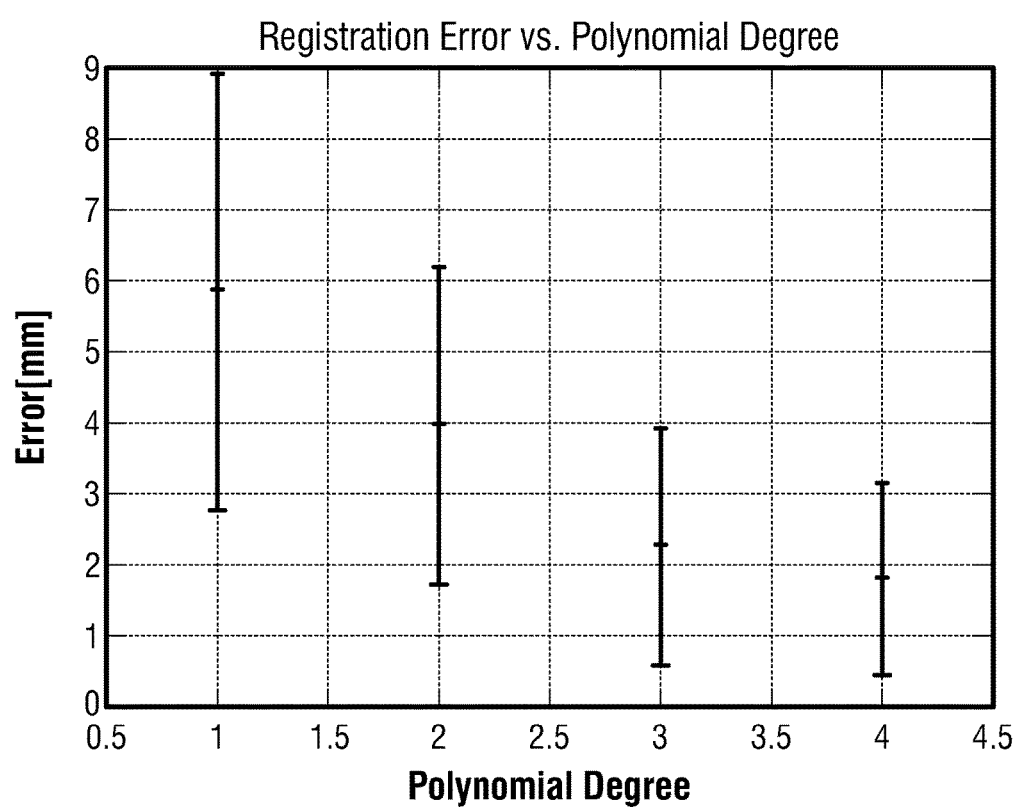

The mean registration errors are shown with confidence levels of two standard deviations on the graph of FIG. 12. Note that both left and right lungs were used for registration.

The polynomial degree and element choice is determined by model accuracy specifications.

CONCLUSIONS

Tissue deformations during the breathing cycle can be described using a low number of degrees of freedom with acceptable accuracy. The transformation can be reproduced using a small number of control points.

It is proven that a specific patient breathing motion can be modeled using the preliminary constructed static "breathing pattern" matrix and a rigid transformation 4×4 matrix dynamically defined from the specific patient.

The "breathing vectors" correction technique can be successfully used during electromagnetic bronchoscopy procedures to reduce localization errors. However, additional data sets are needed if method verification is desired.

It is possible to reproduce the behavior of about 200 breathing vectors by a reduced number of 20 vectors. When approximating the breathing motion by a third order polynomial, 60 (20×3) degrees of freedom should be determined. Hence, there is a system of 20 linear equations, which means about 200 breathing vectors throughout the lungs can be reduced to a 3D vector field determined by just 20 vectors.

Using a simple linear transformation 4×4 in conjunction with a known preliminarily constructed constant 20×3 matrix, it is possible to model the breathing motion of a patient significantly, reducing the registration error.

However, the ability of polynomials to recover anatomical shape variability is often quite limited because they can model only global, not local, shape changes. Additionally, higher order polynomials tend to introduce artifacts, such as oscillations. Therefore, the current method may be improved using other known techniques, such as B-Splines, Thin-Plate Splines, basis functions and others. Introduction of additional deformable component to current algorithm is expected to improve the accuracy of the model. Using a weighting function may also be considered.

The other related issue deals with possible outlier removal. For example the outliers can be determined with regard to their correlation with registration data set and filtered out. Such filtering is essential for breathing motion generic model generation.

Non-uniform distribution of points is a problem that should be also addressed during while modeling the breathing cycle. One possible solution is to use the same points several times in the data set in order to assign them more weight in the algorithm.

There is a high variability of the breathing models generated from different patients by mean of the errors after performing cross-validation analysis. It is expected to find more patients representing "global breathing motion pattern" similar to Patient7 in this study. Assuming the sufficiently accurate and compatible data sets the fusion (or averaging) of several patients may be considered to get more robust results.

It is concluded from the graphs that the error distributions are Rayleigh distribution.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of modeling lung movements due to breathing in a patient comprising:
    acquiring at least one static image of a patient's lungs during a fully inhaled phase of the breathing cycle;
    acquiring at least one static image of a patient's lungs during a fully exhaled phase of the breathing cycle;
    generating at least one electromagnetic field;
    identifying locations of a plurality of points of interest on said static images, wherein location sensors are attached to said patient proximate said points of interest;
    detecting the at least one electromagnetic field with said location sensors;
    determining location data from signals received from said location sensors; and
    using said location data to model the lung movements by predicting mathematically locations of said plurality of points of interest at phases of the breathing cycle between said fully inhaled and fully exhaled phases of the breathing cycle.

2. The method of claim 1 wherein said acquiring at least one static image of a patient's lungs during a predetermined phase of the breathing cycle comprises acquiring a static image at a phase in the breathing cycle that is between inhalation and exhalation.

3. The method of claim 1 wherein said acquiring at least one static image of a patient's lungs during a predetermined phase of the breathing cycle comprises acquiring a static image at a phase in the breathing cycle that is between exhalation and inhalation.

4. The method of claim 1 wherein said acquiring at least one static image of a patient's lungs during a predetermined phase of the breathing cycle comprises acquiring a static image at a phase in the breathing cycle that is between inhalation and exhalation and acquiring a second image in at a phase in the breathing cycle that is between exhalation and inhalation.

5. The method of claim 1 wherein identifying locations of a plurality of points of interest on said at least one static image comprises identifying, on said at least one static image, a plurality of bifurcations in the airways.

6. The method of claim 1 wherein predicting, mathematically, locations of said plurality of points of interest at phases of the breathing cycle other than said predetermined phase comprises developing a mathematical algorithm that models the lung movement of the patient.

7. The method of claim 1 wherein predicting, mathematically, locations of said plurality of points of interest at phases of the breathing cycle other than said predetermined phase comprises calculating a polynomial transformation.

8. The method of claim 1 wherein predicting, mathematically, locations of said plurality of points of interest at phases of the breathing cycle between said fully inhaled and fully exhaled phases of the breathing cycle comprises:
    measuring movement due to breathing at a plurality of points in a plurality of patients;
    averaging the measurements;
    creating a 3-dimensional vector field representative of average movements in the lungs; and
    applying a vector corresponding to an area of interest in the lung to said at least one image in order to predict a location of said area of interest at a given point in the breathing cycle.

9. The method of claim 1 wherein predicting, mathematically, locations of said plurality of points of interest at phases of the breathing cycle other than said predetermined phase comprises creating a skeletal tree of the lungs and modeling the skeletal motion of the lungs.

* * * * *

UNITED STATES PATENT AND TRADEMARK OFFICE
CERTIFICATE OF CORRECTION

| | |
|---|---|
| PATENT NO. | : 10,292,619 B2 |
| APPLICATION NO. | : 12/170385 |
| DATED | : May 21, 2019 |
| INVENTOR(S) | : Dorian Averbuch |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2297 days.

Signed and Sealed this
Sixth Day of December, 2022

Katherine Kelly Vidal
*Director of the United States Patent and Trademark Office*